(12) United States Patent
Graham

(10) Patent No.: US 8,029,453 B2
(45) Date of Patent: Oct. 4, 2011

(54) APPARATUS AND METHOD FOR REDUCTION, CORRECTION AND/OR REVERSAL OF ABERRANT CERVICAL, CERVICO-THORACIC, THORACIC, THORACO-LUMBAR, LUMBAR AND LUMBO-SACRAL/PELVIC POSTURES

(76) Inventor: Richard A. Graham, Huntington Beach, CA (US)

( * ) Notice: Subject to any disclaimer, the term of this patent is extended or adjusted under 35 U.S.C. 154(b) by 1510 days.

(21) Appl. No.: 11/455,169

(22) Filed: Jun. 16, 2006

(65) Prior Publication Data
US 2007/0293796 A1 Dec. 20, 2007

(51) Int. Cl.
*A61F 5/00* (2006.01)
(52) U.S. Cl. .................. 602/33; 602/32; 602/35; 602/36
(58) Field of Classification Search .............. 602/32–40, 602/19, 1; 5/621, 622, 648, 650; 128/870
See application file for complete search history.

(56) References Cited

U.S. PATENT DOCUMENTS

| 4,995,378 | A | * | 2/1991 | Dyer et al. ..................... 606/241 |
| 5,232,424 | A | * | 8/1993 | Pearson et al. ................. 482/106 |
| 5,382,226 | A | | 1/1995 | Graham |
| 5,569,176 | A | | 10/1996 | Graham |
| 5,713,841 | A | | 2/1998 | Graham |
| 5,906,586 | A | | 5/1999 | Graham |
| 6,039,737 | A | * | 3/2000 | Dyer ............................... 606/58 |
| D508,566 | S | | 8/2005 | Graham et al. |
| 7,022,094 | B2 | * | 4/2006 | Buckman et al. ............... 602/23 |
| 7,060,085 | B2 | | 6/2006 | Graham et al. |
| 2006/0161087 | A1 | * | 7/2006 | Carter et al. .................... 602/32 |
| 2007/0079415 | A1 | * | 4/2007 | Carlson ............................ 2/2.5 |
| 2009/0118657 | A1 | * | 5/2009 | Saunders et al. ................ 602/32 |
| 2009/0187127 | A1 | * | 7/2009 | Buckman et al. ............... 602/13 |

* cited by examiner

*Primary Examiner* — Kim Lewis
(74) *Attorney, Agent, or Firm* — Walter A. Hackler

(57) ABSTRACT

An orthopedic device includes at least one torque band disposable around a users' body and having opposing ends extending outwardly from the users' body and generally transverse to a user's spine along with apparatus applying counteracting forces to the ends in order to torque the body to the corrective posture. In addition, a support table may be provided along with a cervical device disposed on the table drop leaf and a pelvis/leg/feet carrier slidably disposed on the table. A lumbar sacral unit is disposed on the table between the cervical device and the pelvis/leg/feet carrier and a movable thorax carrier may be disposed on the support table between the sacral unit and the cervical device.

21 Claims, 8 Drawing Sheets

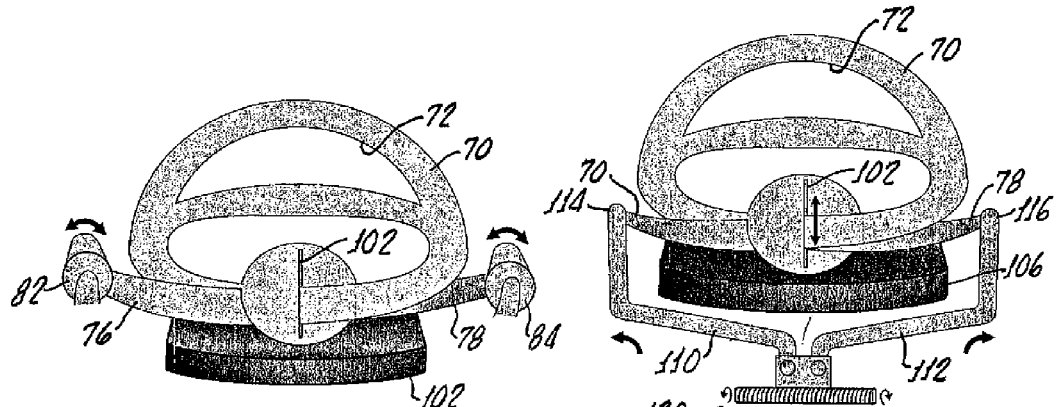
FIG. 15.
FIG. 16.
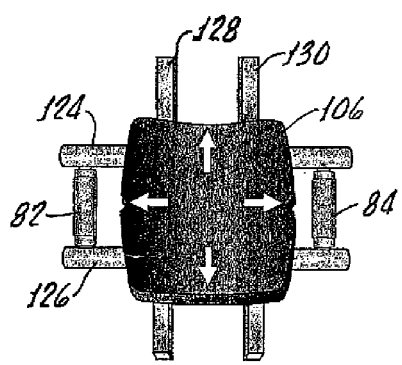
FIG. 17.
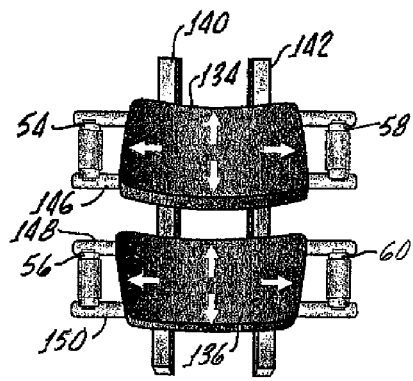
FIG. 18.

APPARATUS AND METHOD FOR REDUCTION, CORRECTION AND/OR REVERSAL OF ABERRANT CERVICAL, CERVICO-THORACIC, THORACIC, THORACO-LUMBAR, LUMBAR AND LUMBO-SACRAL/PELVIC POSTURES

The present invention relates to orthopedic devices and is more particularly directed to apparatus and methods for reduction, correction, and/or reversal of aberrant cervical, cervico-thoracic, thoracic, thoraco-lumbar, lumbar and lumbo-sacral/pelvic postures.

The spinal column is a bony column forming the main structural support of the skeleton of a human being and it consists of bony vertebrae linked by flexible joints and held together by ligaments and flexible gelatinous discs of cartilage. The spinal column of an adult human being consists of thirty-three vertebrae in which the last nine of these are fused to form the sacrum and the coccyx at the back of the pelvis. It is known that the spine has a number of curvatures along the sagittal plane, namely, the cervical and lumbar curvatures in which the spine is convex toward the front of the body and the dorsal and sacral curvatures in which the spine is convex toward the back of the body. These alternating curves provide strength and balance to the body and are essential to allowing a person to walk upright.

The lumbar and cervical curves of the spine normally define forward curves of about 40 and 43 degrees respectively, whereby weight is distributed relatively evenly on individual vertebral surfaces and discs. In individuals with lost or reversed cervical and lumbar spinal curves due to injury, illness, genetic predisposition, habitual microtrauma or simply poor posture, the weight of the body bears forwardly on the soft, non-bony intervertebral discs, inhibiting fluid transfer and causing the discs to wear, dehydrate and degenerate. Over time, these individuals exhibit a significant loss of natural joint movement. Lack of natural movement in the spine over time causes a reduction in the imbibition of nutrient rich fluids that normally lubricate and maintain flexibility of the spine. Without this seepage of fluids into the spinal column, the discs will further dehydrate, which may result in further loss of mobility, crippling and possible nerve damage. It is further noted that the intervertebral discs' indigenous vascular fluid supply disappears at approximately 20 years of age. Thus, active nutrient transport of fluids surrounding the spinal column is particularly important to maintaining spinal health of adults.

In addition to spinal traction devices which are well known for stretching the spine longitudinally in order to restore lost mobility, devices have been developed for either passively or actively restoring the normal curves of the spine to prevent the disabling effects of lost or impaired curvature mentioned hereinabove. Passive devices include, for example, the Spinal Column Correction Device disclosed in U.S. Pat. No. 5,279,310 to Hsein. In this device, a user is strapped to a series of raised supports that define what the normal curvatures of the spine should be. According to the inventor, the weight of the user's body will bear against the raised supports to correct abnormal curvature in the spine. A useful device that actively exercises the normal lordotic, i.e. forward, curves of a spine is disclosed in U.S. Pat. No. 5,382,226 to Graham entitled Inflatable Cervical Traction and Exercising Device, this patent being incorporated herein by this specific reference thereto. In the Graham patent, a device is disclosed which utilizes an inflatable bladder for actively forcing the cervical spine into a forward semi-circular curve. This exercising of the spine promotes fluid imbibition through the spinal vertebrae and intervertebral discs.

U.S. Pat. No. 5,906,586 to Graham provides for a device and method for maintaining spinal health which utilizes a dual action air chamber defining multiple vectors of force to be applied to a spine, particularly to the thoraco-lumbar, lumbar, and lumbo-sacral/pelvic spinal regions. The device gradually lifts and separates the vertebrae in a manner that surpasses the effectiveness and comfort of conventional traction devices and passive spinal correction.

The present invention provides for devices apparatus and methods to multi-directionally decompress, hydrate and simultaneously shape the human spine so that the head and cervical spine are aligned and the cervical spine is lordotically shaped and aligned above the thorax, the thorax is properly shaped and aligned above the lumbar spine and pelvis and the lumbar spine and pelvis is properly shaped and aligned above the legs and feet.

SUMMARY OF THE INVENTION

An orthopedic device in accordance with the present invention includes at least one torque band disposable around the users' body and having opposing ends extending outwardly from the users' body and generally transverse to a users' spine. Apparatus applying counteracting forces to the ends is provided in order to torque the body into a corrective posture.

More particularly, the orthopedic device in accordance with the present invention may include at least one thorax torque band disposable around a users' thorax and having ends extending outwardly from the users' thorax and generally transverse to a users' spine along with apparatus applying counteracting forces to the ends in order to torque the thorax to a corrective position in relation to a users' head/neck and/or lower body.

In addition, the orthopedic device may include a slot disposed in the band which enables crossing of the band with one of the ends passing through the slot. In one embodiment of the present invention two thorax torque bands are provided and disposable in a spaced apart relationship around the users' thorax with each band having opposing ends extending outwardly from the thorax and generally transverse to the users' spine. Separate apparatus is provided corresponding to each band for applying counteracting forces to the ends of each band.

A further embodiment of the present invention includes a thorax vest having loops for guiding each of the bands and each of the bands may be disposed with the slots adjacent to the users' spine in order that the counteracting forces applied to the each band causes the users' ribs to be forced toward the spine and pushed against the spine to correct abnormal posture.

The thorax torque band may be provided with a frontal breast accommodating opening to prevent otherwise uncomfortable pressure against a users' breast.

The apparatus for applying counteracting forces may include, in one embodiment, a pair of motorized rollers, each band and being attached to a corresponding roller for enabling each roller to wrap the band thereabout to apply the counteracting forces hereinabove noted. Alternatively, a pair of torque arms may be provided with each band being attached to a corresponding torque arm with the torque arm, in turn, pulling the ends in opposing directions to apply the counteracting forces.

Still another embodiment of the present invention includes a support table along with a movable thorax carrier disposed on the support table between the band ends for facilitating the torquing of the thorax.

In addition, the support table may include a hinge drop leaf to add a linear decompressive component (as it pulls or dips back) to the EED (EXPANDING ELLIPSOIDAL DECOMPRESSION) produced with the cervical device disposed thereon and securable about a users' head for imparting a desired lordotic shape into the cervical region of the users' spine.

A pelvis/leg/feet carrier may be slidably disposed on the support table and the device may further include at least one pelvic band disposable around a users' pelvis and having ends extending outwardly from the users' body and generally parallel to the users' spine and connected to the pelvis/leg/feet carrier for applying traction to the users' body.

Still another embodiment of the present invention includes a lumbar sacral unit disposed on the support table between a cervical device and the pelvis/leg/feet carrier for enhancing an elliptical arch in the users' lower spine.

BRIEF DESCRIPTION OF THE DRAWINGS

The present invention will be more readily understood in light of the following detailed description when considered in conjunction with the accompanying drawings, of which:

FIG. 15 is an end view of the torque band illustrated with motorized rollers for applying counteracting forces to each band along with a movable thorax carrier;

FIG. 16 is an illustration similar to that shown in FIG. 15 utilizing torque arms attached to corresponding band ends for pulling the ends in opposing directions to apply the counteracting forces hereinabove noted;

FIG. 17 is a plan view of a single thorax carrier showing degrees of movement along tracks;

FIG. 18 is similar to the carrier view of FIG. 17 illustrating the use of two carriers suitable for the use of two thorax bands in a spaced apart relationship;

DETAILED DESCRIPTION

Figure 1:
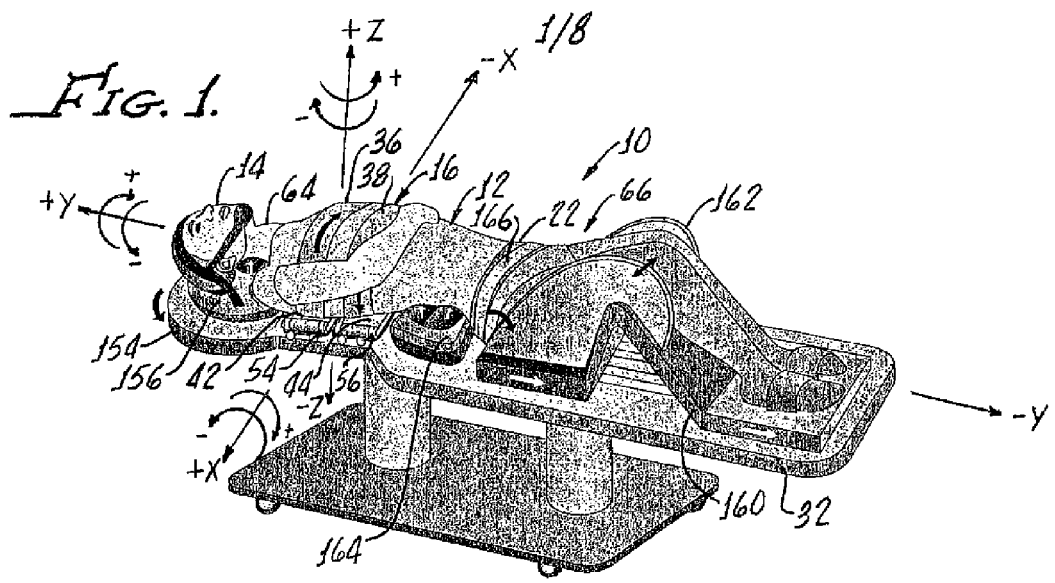
FIG. 1 is a perspective view of an orthopedic device in accordance with the present invention generally showing a pair of bands disposed around a users' body torqued by motorized rollers disposed on the table along with a cervical EED device, lumbar and sacral unit and a pelvis/leg/feet carrier slidably disposed on the table along with an indication of a Cartesian coordinate system showing various degrees of motion hereinafter described in connection with the manipulation of the users' body.

With reference to FIG. 1, the purpose of the orthopedic device in accordance with the present invention is to multi-directionally decompress, hydrate and simultaneously shape the human spine of a user 12 so that the head 14 and cervical spine (not shown) are aligned and the cervical spine is lordotically shaped and aligned above the thorax 16, the thorax 16 is properly shaped and aligned above the lumbar spine (not shown) and pelvis and the lumbar spine and pelvis 22 is properly shaped and aligned above the legs and feet.

The most common aberrant posture exists when the center mass of the head 14 and cervical spine, as one unit, is positioned too far forward of the thorax (+z translation) accompanied by reversal or reduction of the lordotic cervical curve. This aberrant posture is often accompanied by posterior translation of the thorax 16 in relation to the lumbar spine and pelvis 22 (−z translation), forcing the lumbar spine into hyper-lordosis. Posterior malposition of the thorax 16 (−z translation) is often complicated by its lateral translation, rotation, and lateral flexion. Since the thorax 16 carries most of the mass, its aberrant posture can greatly affect the entire spine. Scoliosis, a condition in which the spine laterally deviates from the midline, is most often found in patients exhibiting loss or reversal of the cervical lordotic curve. Often, the greatest deviation from the midline is measured in the thoracic spine.

The present invention relies on the previously patented technology of Expanding Ellipsoidal Decompression or EED, by Dr. Graham, namely U.S. Pat. Nos. 5,382,226, 5,569,176, 5,713,841, 5,906,586, 7,060,085, and D508,565. All of these patents are incorporated herewith in their entirety by this specific reference thereto. Modalities built on these U.S. patent have proven, in pre and post radiographs and in general practice, to reliably reduce and correct damage to the cervical and lumbar lordotic curves while simultaneously decompressing and hydrating the intervertebral discs.

An added benefit of restoring the lordotic curve in the cervical spine, using EED, has been to reposition the center of skull mass, posterior (−z), above the mid cervical vertebra and the thorax. Thus, eliminating or reducing forward head posture. IN the lumbar spine, the employment of EED based on the aforementioned patients, has clinically shown the added benefit of not only restoring the natural elliptical shape of the lumbar spine when it has been lost but also to decrease the magnitude of lordotic arc when it is hyper-lordotic. The reduction of the hyper-lordotic lumbar curve is accomplished by opposing elliptical pneumatic forces described in U.S. Pat. No. 5,906,586 VECTORED PNEUMATIC JOINT SEPARATOR. The reduction of the hyper-lordotic lumbar curve helps align the thorax above the lumbar and pelvic spine.

The present invention 10 places the EED art into a platform or table, 32, allowing it to be utilized in conjunction with the forceful repositioning of the thorax. Specifically, the repositioning of the apex(s) of the thoracic kyphotic curve into positions that reverse aberrant postures and decompress the thoracic spine and discs.

An important feature of the present invention is the use of torque bands 36, 38 preferably disposable about the thorax 16 of the users' body 12 and having ends 42, 44, 46, 48 extending outwardly from the users' body 12 and generally transverse to the users' spine (see FIGS. 2-6). Motorized rollers 54, 56, 58, 60 provide apparatus for applying counteracting forces to the ends 42, 46 and 44, 48 respectively in order to torque the body 12 and thorax 16 into a corrective posture in relation to a users' head 14, neck 64 and lower body 66. The rollers 54, 56, 58, 60 may include internal motors commercially available or may be externally driven by conventional drives (not shown).

The thorax torquing is illustrated in FIGS. 3-6 by utilizing counteracting forces causing torque movement as illustrated by the arrows.

Figure 3:
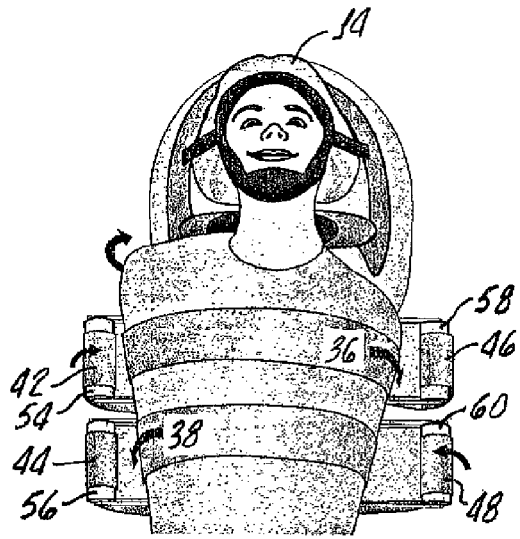
FIGS. 3-6 illustrate various translations and rotations of a users' body provided by the thorax torque bands in accordance with the present invention.

FIG. 3 shows right thorax translation (−x axis translation), left rotation (+y axis rotation), left lateral flexion (+z axis rotation), and right lower thorax rotation (−y axis rotation), see FIG. 1 for the reference translations and rotation coordinates.

Figure 4:
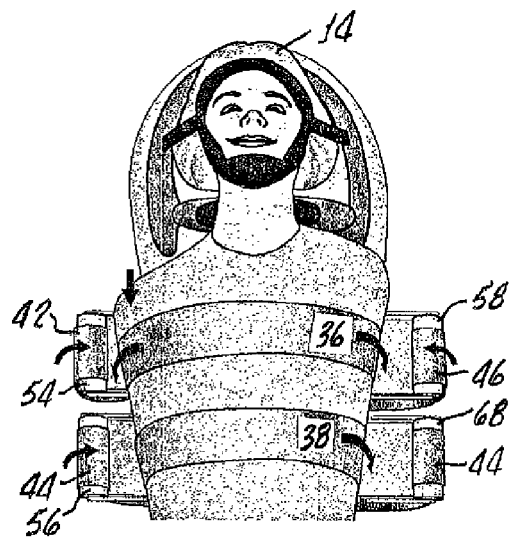

FIG. 4 illustrates right thorax translation (−x axis translation), right rotation (−y axis rotation), right lateral flexion (+z axis rotation), and left lower thorax rotation (+y axis rotation).

Figure 5:
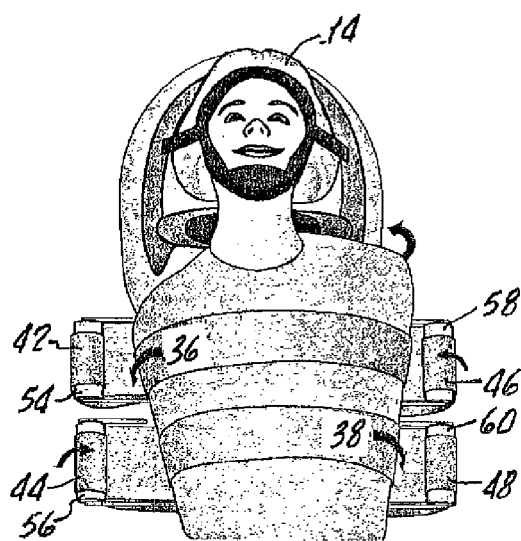

FIG. 5 illustrates left thorax translation (+x axis translation), right rotation (−y axis rotation), right lateral flexion (+z axis rotation), and left lower thorax rotation (+y axis rotation).

Figure 6:
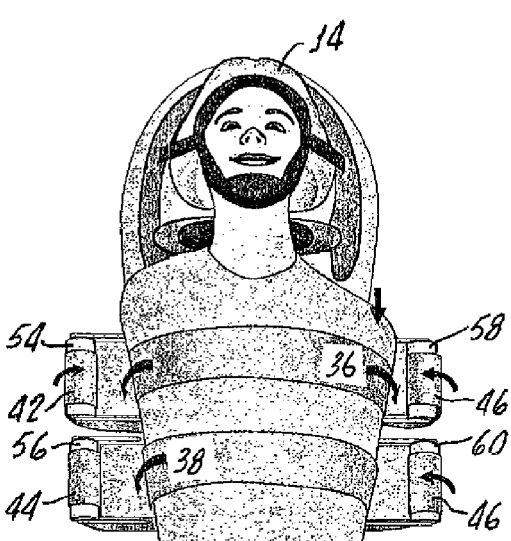

FIG. 6 illustrates left thorax translation (+x axis translation), left rotation (+y axis rotation), left lateral flexion (−z axis rotation), and right lower thorax rotation (−y axis rotation).

With reference to FIGS. 7-10, there is shown thorax torquing utilizing a thorax torque band 70 having a frontal breast accommodating opening 72 with opposing ends 76, 78 extending outwardly from the users' body 12 and generally transfers to a users' spine (not shown).

As shown, the ends 76 are wrapped around motorized rollers 82, 84 in order to effect thorax torque.

Figure 7:
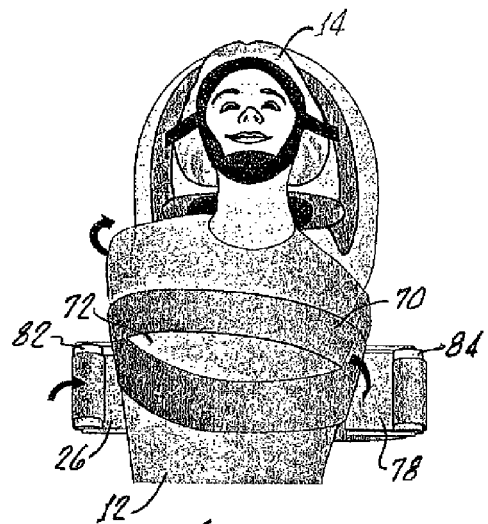
FIGS. 7-10 further illustrate a torquing of a users' thorax utilizing a thorax torque band including a frontal breast accommodating opening.

FIG. 7 illustrates right thorax translation (−x axis translation), left rotation (+y axis rotation), and left lateral flexion (−z axis rotation).

Figure 8:
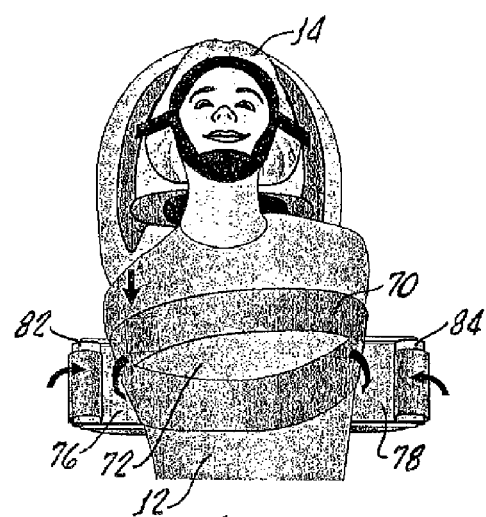

FIG. 8 illustrates right thorax translation (−x axis translation), right rotation (−y axis rotation), and right lateral flexion (+z axis rotation).

Figure 9:
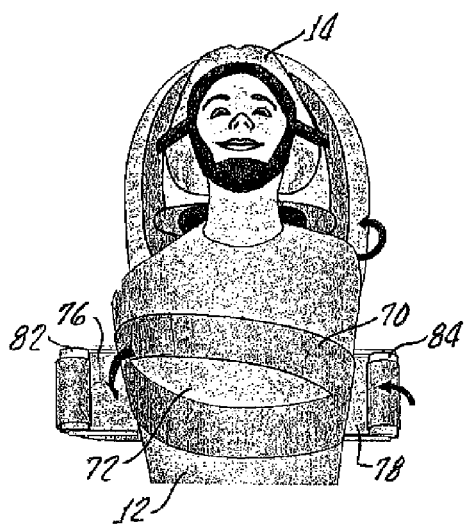

FIG. 9 illustrates left thorax translation (+x axis translation), right rotation (−y axis rotation), and right lateral flexion (+z axis rotation).

Figure 10:
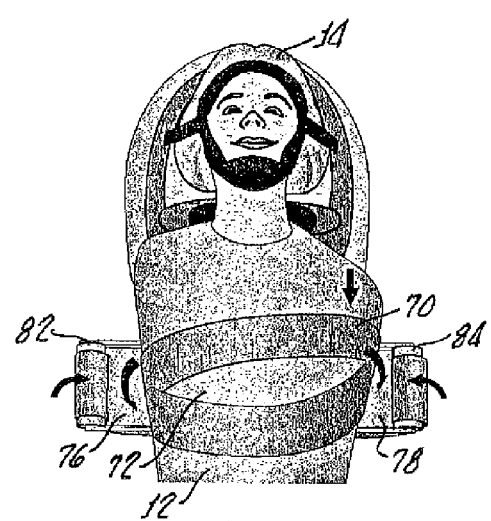
Figure 11:
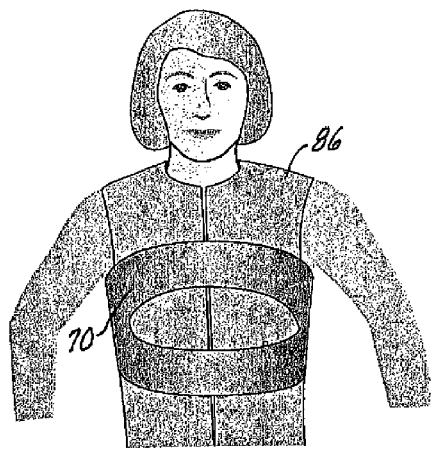
FIGS. 11 and 12 further illustrate the torque band with the frontal opening and also illustrate a slot disposed in the band enabling crossing of the band with one of the ends passing through the slot, both ends extending generally perpendicular to the users' body.

FIG. 10 illustrates left thorax translation (+x axis translation), left rotation (+y axis rotation), and left lateral flexion (−x axis rotation).

As illustrated in FIGS. 11-14, the thorax vest 86, 88 may be provided along with loops 92, 94, 96, 98, 100, 102 for guiding each band. This arrangement facilitates accurate placement of the torque bands 70 about the users' thorax.

Figure 13:
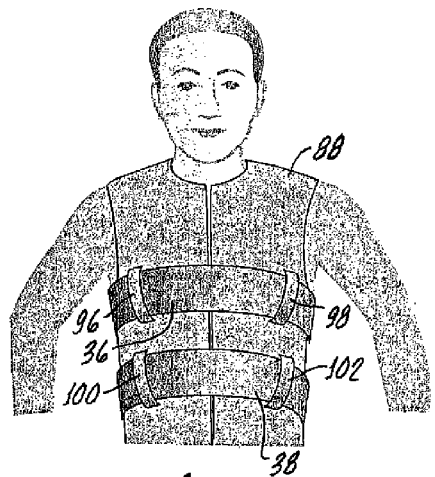
FIGS. 13 and 14 illustrate a thorax vest suitable for use with the thorax torque bands along with loops for guiding each of the band, FIG. 14 illustrating slots and the bands for accommodating band end crossings on the chest of the user.
Figure 14:
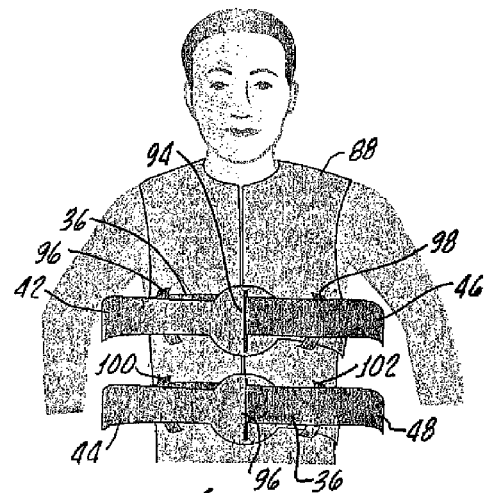
Figure 19:
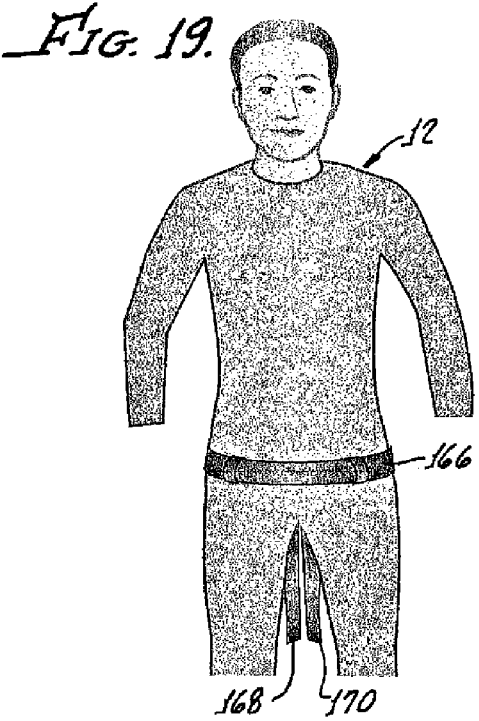
FIGS. 19-22 illustrate placement of a pelvic band disposable around the users' pelvis.
Figure 20:
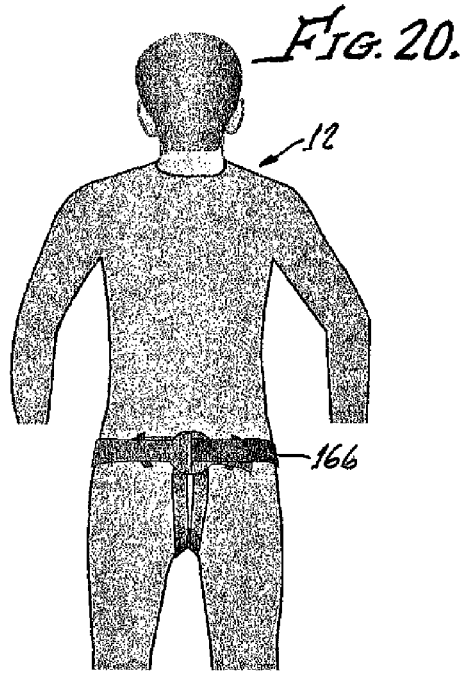
Figure 21:
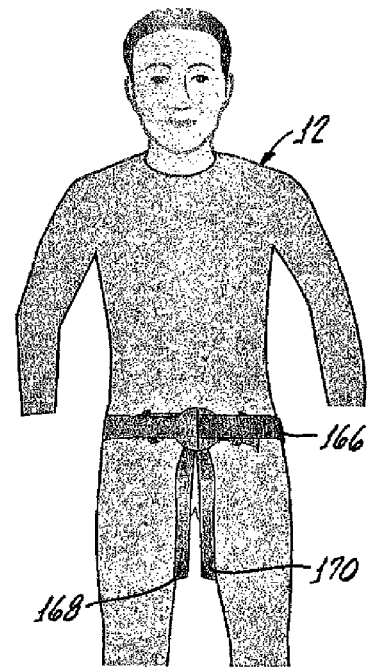
Figure 22:
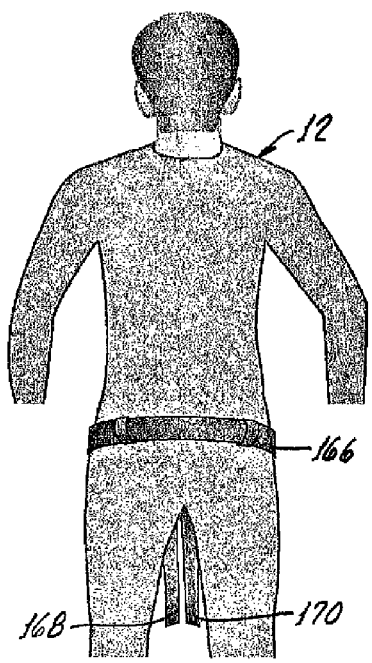

As best shown in FIG. 14, slots 94, 96 may be disposed in the bands 36, 38 respectively which enables crossing of the band 36, 38 with one of the ends 46, 48 passing through these slots 94, 96. In FIG. 14, the slots are arranged over the users' chest whereas, as illustrated in FIG. 13, the slots are disposed adjacent the users' spine, not shown. This latter arrangement enables counteracting forces applied to each band to cause the users' ribs to be forced toward the spine and to act as pushrods against the spine to correct abdominal posture.

Figure 12:
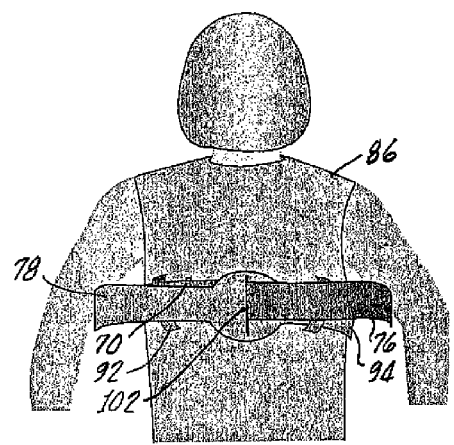

Similarly, as shown in FIG. 12, the band 70 includes a slot 102 and as more clearly illustrated in FIGS. 15 and 16, showing is an end view of the thorax band 70 as it may be disposed over a movable thorax carrier 106.

An alternative embodiment apparatus for applying counteracting forces to the end 76, 78 is shown in FIG. 16 in which torque arms 110, 112 have ends 114, 116 attached to band ends 76, 78 respectively. The arms may be driven by any conventional mechanism illustrated at 120 in FIG. 16.

The thorax carrier 106 show in a end or tunnel view in FIG. 15 is illustrated in FIG. 17 and is mounted on tracks 124, 126, 128, 130 in a conventional matter for enabling translational movement, as illustrated by the arrows. The user disposes his back onto the carrier 106 to facilitate the torquing by the band 70, as hereinabove described.

Similarly, two carriers 134, 136 may be utilized with bands 36, 38 and are disposed between rollers 54, 58 and 56, 60 respectively on tracks 140, 142, 144, 146, 148, 150 in a conventional manner for enabling translational movement as illustrated by the arrows.

With reference again to FIGS. 1-2A and 2B, the support table 32 includes a drop leaf 154 to add a linear decompressive component to the EED produced with the cervical device 156 disposed thereon and securable about a users' head for parting a desired lordotic shape into the cervical region of the users' spine. The cervical device 156 is described in U.S. Pat. Nos. 5,569,176, 5,713,841, and 5,906,586 is incorporated herein by reference and accordingly further description is not necessary in the present application for the sake of brevity.

With continued reference to FIGS. 1, 2A and 2B, a device 10 further includes a leg carrier 160 slidably disposed in a conventional manner on the table 32 for providing pelvis translation, as will be hereinafter described in greater detail. In addition, in order to prevent or control twisting of the lower body 66, knee fenders 162 may be fixed to the leg carrier 160.

Further, a lumbar sacral unit 164 disposed on the support table 32 between the cervical device 156 and carrier 160 is provided for enhancing an elliptical arch in the users' lower spine. The lumbar sacral unit 164 is described in U.S. Pat. No. 5,713,841, U.S. Pat. No. 5,906,586, and U.S. Pat. No. 7,060,085 which are incorporated herewith for the purpose of describing of this unit and accordingly no further description is provided herein for the sake of brevity.

Figure 2A:
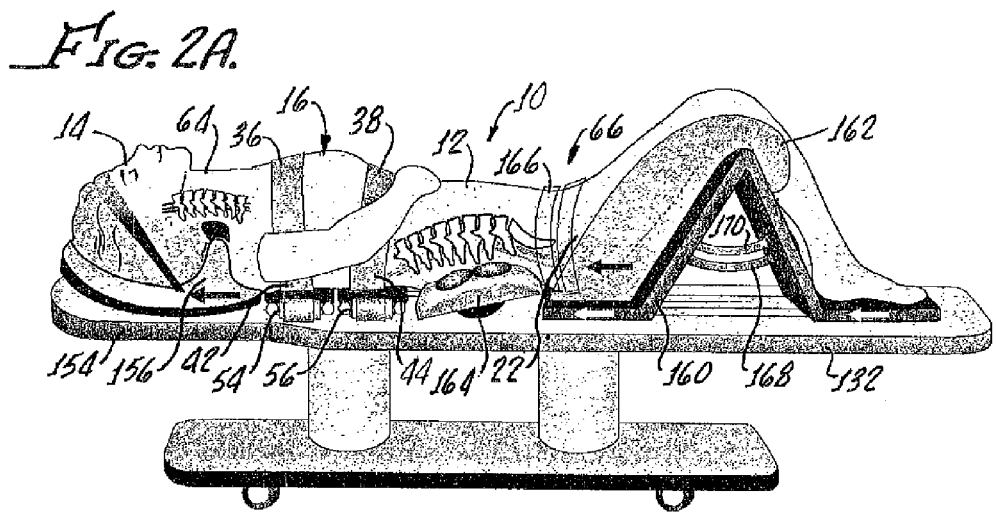
FIG. 2A is a side view of the device shown in FIG. 1 with the device in a deflated neutral position.
Figure 2B:
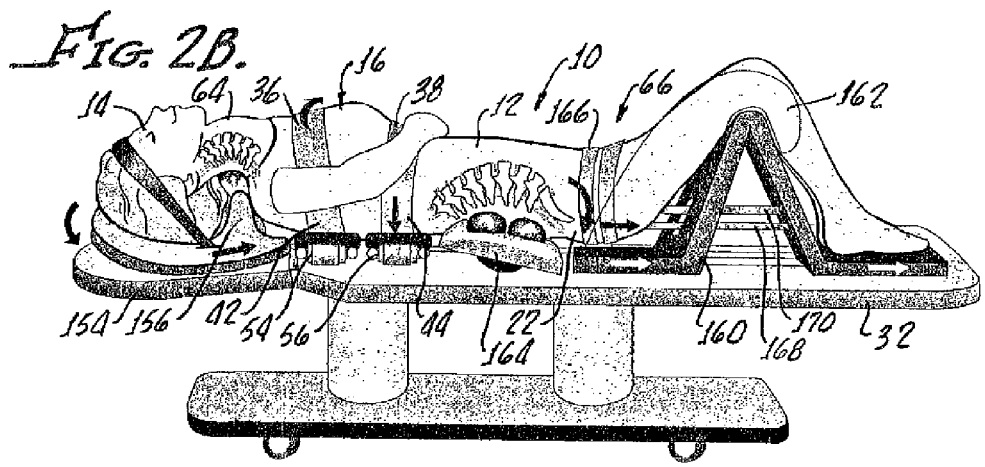
FIG. 2B is a view similar to that shown in FIG. 2A showing the inflation of the cervical device along with the lumbar sacral unit and movement of the carrier to provide pelvic sling action.

Pelvic bands as shown in FIGS. 19-22 may be provided with ends 168, 170, attachable to the carrier 160, as shown in FIGS. 2A and 2B, with the operation thereof hereinafter described in greater detail.

Figure 23:
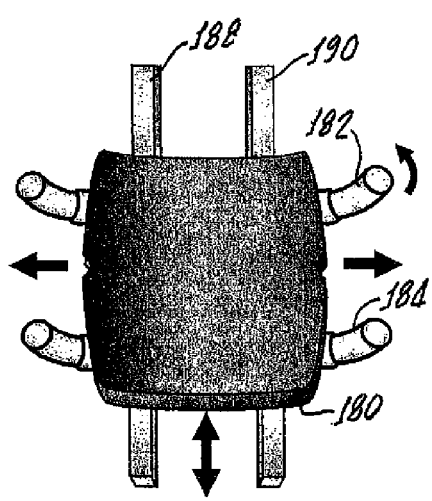
FIGS. 23-24 illustrate a thorax carrier moveably mounted on concave rails.
Figure 24:
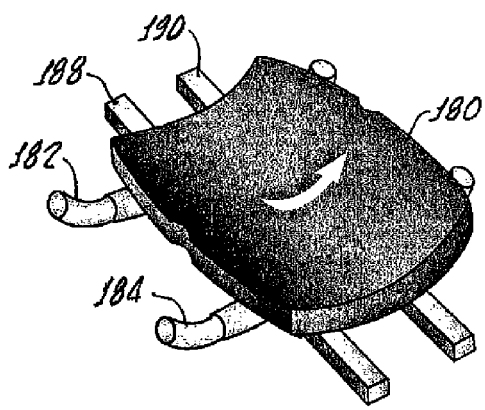

An alternative thorax carrier 180 is shown in FIGS. 23-24 mounted on concave rails 182, 184. Motorized movement of the carrier torquing of the users' thorax, not shown in FIGS. 23-24, is indicated by the carriers. Thorax bands, also not shown in FIGS. 23-24, secure the users' thorax thereby enabling the torquing or rotational action by the carrier 180. Rails 188, 190 enable translational movement of the carrier 180. The carrier may be motorized in any conventional manner.

Figure 25:
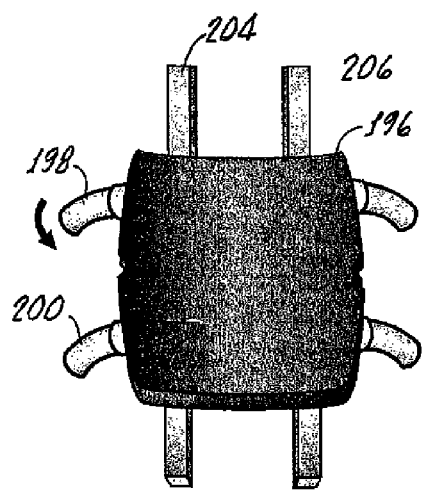
FIGS. 25-26 illustrate a thorax carrier movably mounted on convex rails.
Figure 26:
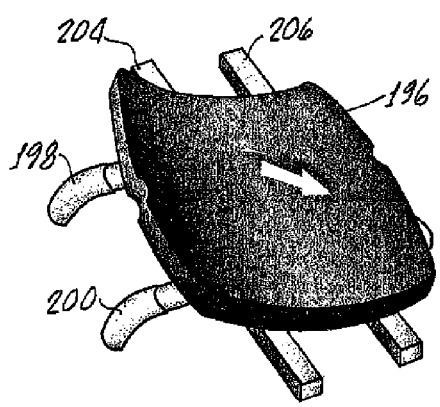

FIGS. 25-26 illustrate a carrier 196 mounted on convex rails 198, 200, with motorized movement of the carrier 196 causing thorax torquing or twisting. Translational movement of the carrier 196 is enabled by the rails 204, 206.

Figure 27:
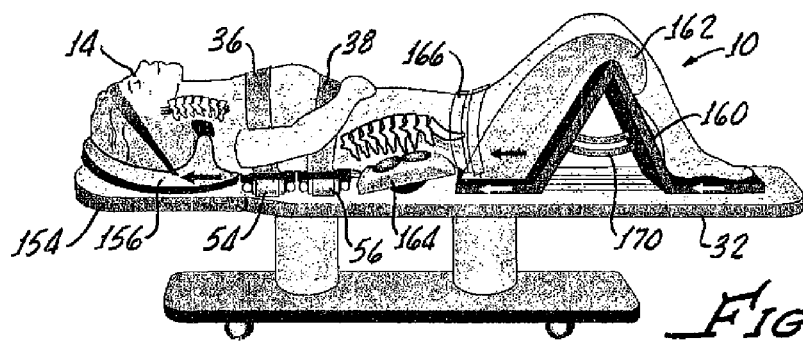
FIGS. 27-30 illustrate the method of multi-directionally decompressing, hydrating and shaping the human spine in accordance with the present invention as will be hereinafter discussed in greater detail.
Figure 28:
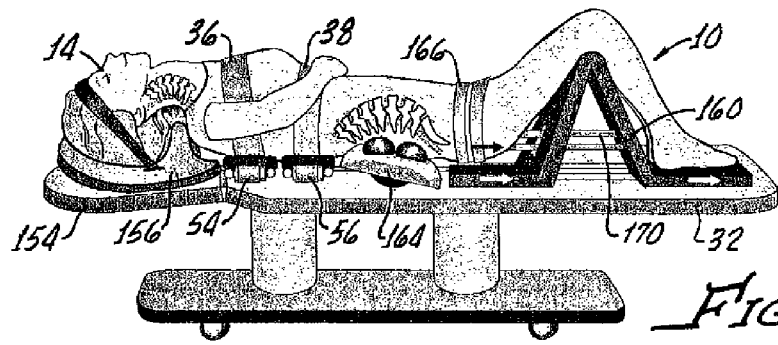

FIGS. 27-30 illustrate operation of the device 10 and method in accordance with the present invention. FIG. 27 shows a deflated neutral position, 28 shows a simultaneous combination of superior and inferior straight pelvic sling pulls yielding a neutral torque.

Figure 29:
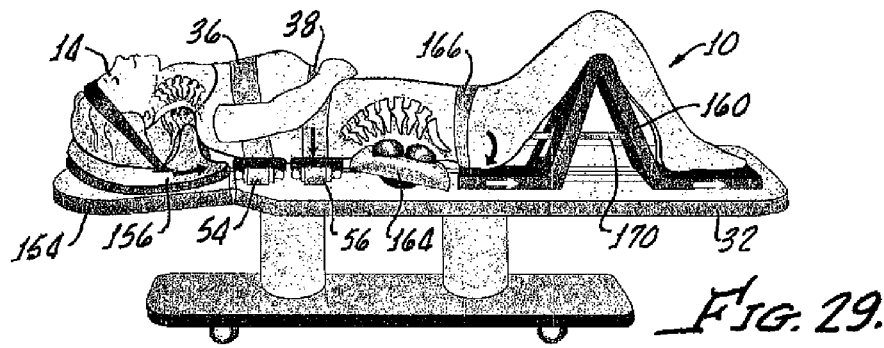
Figure 30:
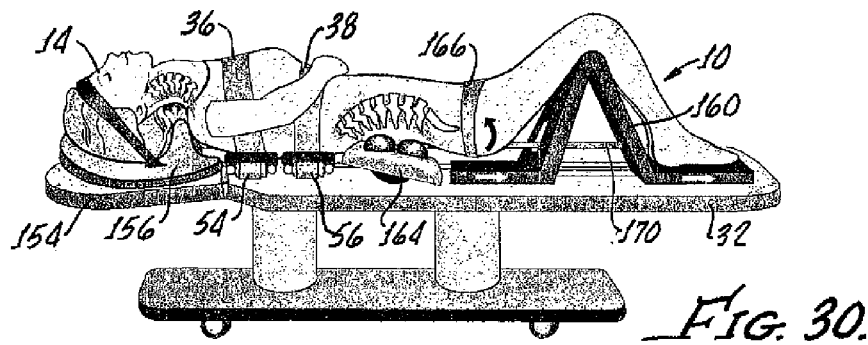

FIG. 29 shows a superior pelvic sling pull with a single straight pull from the top yielding a downward torque and FIG. 30 shows an inferior pelvic sling pull with a single straight pull from the bottom yielding an upward torque, as indicated by the arrows.

As hereinabove noted, the purpose of the invention is to multi directionally decompress, hydrate and simultaneously shape the human spine so that the head and cervical spine are aligned and the cervical spine is lordotically shaped and aligned above the thorax, the thorax is properly shaped and aligned above the lumbar spine and pelvis and the lumbar spine and pelvis is properly shaped and aligned above the legs and feet.

As hereinabove noted, present invention 10 places the EED art into the platform 32 allowing it to be utilized in conjunction with the forceful repositioning of the thorax. Specifically, the repositioning of the apex(s) of the thoracic kyphotic curve into positions that reverse aberrant postures and decompress the thoracic spine and discs.

Methods of Thorax Repositioning:

1. Motorize Torque Sling: A band or bands 36, 38 of material are affixed around the thorax 16 so that they lie across the chest, wrap around and cross/intersect behind the back, or lie across the back, wrap around and cross/intersect in front of the chest, depending on the aberrant posture to be reversed. With the cervical and or the lumbar spine under EED, motorized directional forces are applied to each end of the bands 36, 38, unilaterally and or bilaterally, thus moving the thorax 16 into a corrective posture in relation to the head/neck 14, 64 and or lower body 66. The torque quality of the force imparted to the thorax 16 with the torque band 36, 38 crossing/intersecting behind the back is particularly valuable in reversing thoracic rotation (+, −y-axis rotation), lateral translation (+, −x-axis rotation) and lateral flexion (+, −z axis rotation).

By intersecting the free ends of the bands behind the back and applying force, the ribs are pulled toward the spine thus using the ribs as push rods against vertebral demi-facets to correct abnormal posture. When Torque Slings 36, 38 cross in front of the body, ribs are pulled away from their demi-facets and the "push rod" effect is lost. (In certain rib dislocation configurations this maybe a plausible method). In either application, allowing the free ends of the torque bands 36, 38 to pass through each other and at the point of intersection 94, 96 (see FIG. 14) and pulling from the same horizontal level stabilizes the force applied to the thorax 16. Allowing force to be applied to the bands 36, 38 at unequal horizontal levels (in relationship to each other) adds an additional force vector to the thorax 16 that can be used to ameliorate lateral flexion (+, −z-axis rotation). Corrective positions produced by the Motorized Torque Sling are held and released in conjunction with expansion and contraction of the cervical and lumbar pneumatic units.

Various methods may be used to apply counteracting force to the torque bands 36, 38. For example, motorized rollers 54, 56, 58, 60 hereinabove described and the motorized torque arm mechanism 120 shown in FIG. 16.

A 4-roller system and/or a 4-torque arm system as opposed to dual systems allows the thorax to be torqued at two levels in two opposing directions and or to be torqued at two levels simultaneously, which is very useful in patients with complex scoliosis. The torque slings or bands 36, 38 can be positioned directly around the patient or applied through a torque vest (see FIGS. 13-14). The user or patient 12 is positioned on a mobile thoracic carrier (motorization of carrier not necessary) as the motorized torque slings are activated to reverse specific cervico-thoracic, thoracic and thoraco-lumbar spinal aberrances.

The carriers 106, 134, 136 (FIGS. 15-18) may be motorized in any suitable manner and are shaped to cradle the thoracic spine and fit between the head/neck unit 156 and thoraco-lumbar unit 162. The carrier(s) 106, 134, 136 are adjustable vertically along the length of the thorax. The carrier(s) move laterally right and left on the railing system 124, 126. The carrier's top-plate is adjustable on the thoracic y-axis, that is, it can be tipped + or − along the patient's y-axis (counter clockwise or clockwise). This adjustment will also reverse thoracic rotation and may be used in addition to or lieu of concaved and convex rails 180, 182, 198, 200. The carrier's top-plate is also rotationally adjustable on the thoracic z-axis to reverse + and −z-axis rotation.

Dual pelvic slings 166 may be attached to pelvis and pelvic/leg/feet carrier, [over top of pelvis (superior) and under bottom of pelvis (inferior)] to pelvic area. This allows the pelvis to travel with the legs and feet adding combinations of + and − pelvic x-axis rotations to the −y-axis pelvic translation produced by the linier travel of the pelvic/legs/feet carrier.

a) If the force of the carrier's linear travel is applied exclusively to the anterior or top sling, the pelvis is linearly decompressed (−y axis translation) and rotated forward (+x axis rotation).

b) If the force of the carrier's linear travel is applied exclusively to the inferior or bottom sling, pelvis is linearly decompressed (−y axis translation) and rotated back (−x rotation).

c) If the force of the carrier's linear travel is applied simultaneously to both slings, −x and +x pelvic rotations cancel each other out and the pelvis receives a balanced −y axis decompressive force.

With reference to FIGS. 27-30 [1] the pelvis, legs and feet travel forward (−y translation) on a linear path, [2] the lumbo-sacral unit rocks forward (+x rotation) and stops, as [3] the pneumatic head/neck unit tilts back (−x rotation) and [4] drops down (−z translation) and with the pelvis/legs/feet carrier still traveling forward (−y pelvis translation), [5] the thoracic unit causes the thorax to shift laterally right or left (−x, or +x translation), [6] rotate on the y-axis counter-clockwise or clockwise (+y, −y rotation), [7] laterally flex right or left (+z, −z rotation) and [8] the lower thoracic spine to counter rotate. The pelvic/leg/feet carrier then reverses direction, the pneumatic lumbo-sacral unit rocks back (−x rotation), the thoracic unit and head/neck unit simultaneously return to their starting positions and the pneumatic cervical and lumbar units deflate.

Note: The tilting down and away (−x rotation) and (−z translation) of the cervical headpiece and the forward travel of the pelvis, legs and feet lends a linier decompressive component to the pneumatic cervical and lumbar EED units. Thus, the patient experiences simultaneous Expanding Ellipsoidal Decompression and Linier Decompression.

A key to the uniqueness and therapeutic value of this complex of linked movements is that they are performed with the cervical spine and lumbar spine powerfully decompressed and shaped into their essential lordotic configuration. That is, the upper and lower spine is under (Under EED).

Other Features:

A. Pelvic release (drop) at end of forward rocker travel. As the pelvis rocks forward the last approximately 25 to 50% of travel is suddenly released thus overcoming The Moment of Inertia at the apex of arc.

B. Head unit release (drop) as unit dips back and down. As the head rocks back and down, the last approximately 25 to 50% of travel is suddenly released thus overcoming The Moment of Inertia at the apex of arc.

C. Thigh support unit locks the pelvis, legs and feet of linier travel.

D. Dual pelvic slings are attached to pelvis and pelvic/leg/feet carrier, [over top of pelvis (superior) and under bottom of pelvis (inferior)] to pelvic area. This allows the pelvis to travel with legs and feet adding combinations of + and − pelvic x rotation to the −y pelvic translation produced by the linier travel of the pelvic/legs/feet carrier. If the force of the carrier's linear travel is applied exclusively to the anterior sling, the pelvis is linearly decompressed and rotated forward (+x axis rotation). If the force of the carrier's linear travel is applied exclusively to the inferior or bottom sling, pelvic is linearly decompressed and rotated back (−x rotation). If the force of the carrier's linear travel is applied simultaneously to both slings, −x and +x pelvic rotations cancel each other out and the pelvis receives a balanced −y axis decompressive force. The force or forces selected by the clinician are compounded by the fact that the lower spine is being elliptically expanded and decompressed by the patented lower back unit. That is, the lower spine is under Expanding Ellipsoidal Decompression (EED).

In accordance with the present invention Expanding Ellipsoidal Decompression (EED) from within the lordotic concavity has proven on video fluoroscopic studies to decompress the intervertebral discs in lordotic areas of the spine in A to P ratio of separation that is much more consistent with the body's natural anatomy than can be achieved with linear traction. Expanding ellipsoidal decompression achieves remarkable, often immediate, spinal range of motion recovery. Unlike linear traction, ellipsoidal decompression enhances both the essential circular shape of the cervical spine and the essential elliptical shape of the lumbar spine and therefore does not compromise the postural curves.

Although there has been hereinabove described a specific intervertebral disc hydrating, spine exercising and postural correcting device in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. An orthopedic device comprising:
   a support table;
   at least one torque band disposable around a user's body and having opposing ends adapted to extend outwardly from the user's body and generally transverse to a user's spine;
   a moveable thorax carrier disposed on said support table and between the band ends; and
   apparatus applying counteracting forces to the ends in order to torque the body into a corrective posture; and
   a thorax vest having a loop for guiding each band; and
   a slot, disposed in the band enabling crossing of the band with one of the ends passing through said slot.

2. The orthopedic device according to claim 1 further comprising two thorax torque bands disposable in a spaced apart relationship around the user's thorax, each band having opposing ends adapted to extend outwardly from the thorax and generally transverse to the user's spine and separate apparatus, corresponding to each band, applying counteracting forces to ends of each band.

3. The orthopedic device according to claim 2 wherein each band includes a slot enabling crossing of the ends of each band with one of the ends of each band passing through a corresponding slot.

4. The orthopedic device according to claim 3 wherein each band is disposed with the slots adjacent the user's spine and attached so that applied force pulls from under the spine and against the lateral angle of the ribs in order that the counteracting forces applied to each band cause the user's ribs to be forced toward the spine in a push rod fashion to correct abnormal posture.

5. The orthopedic device according to claim 1 wherein the apparatus includes a pair of motorized rollers, each band end being attached to a corresponding roller, each roller wrapping the band thereabout to apply the counteracting forces.

6. The orthopedic device according to claim 1 wherein the apparatus includes a pair of torque arms, each band end being attached to a corresponding torque arm, the torque arms pulling the ends in opposing directions.

7. The orthopedic device according to claim 1 wherein said support table comprises a hinge drop leaf and the device further comprises a cervical device disposed on the drop leaf and securable about a user's head for imparting a desired lordotic shape into the cervical region of the user's spine.

8. The orthopedic device according to claim 7 further comprising a pelvis/leg/feet carrier slidably disposed on said support table.

9. The orthopedic device according to claim 8 further comprising at least one pelvic band disposable around a user's pelvis and having ends adapted to extend outwardly from the user's body and generally parallel to a user's spine and connected to the pelvis/leg/feet carrier for applying traction to the user's body.

10. The orthopedic device according to claim 8 further comprising a lumbar sacral unit disposed on said support table between the cervical device and the pelvis/leg/feet carrier for enhancing an elliptical arch in the user's lower spine.

11. An orthopedic device comprising:
    a support table having a hinge drop leaf;
    a cervical device disposed on the drop leaf and securable about a user's head for imparting a desired lordotic shape into the cervical region of the user's spine;
    a pelvis/leg/feet carrier slidably disposed on said support table;
    a lumbar sacral unit disposed on said support table between the cervical device and the pelvis/leg/feet carrier for enhancing an ellipsoidal arch in the user's lower spine;
    a movable thorax carrier disposed on said support table between the sacral unit and said cervical device;
    at least one thorax torque band disposed over the thorax carrier and disposable around the user's thorax and having opposing ends adapted to extend outwardly from the user's thorax and generally transverse to the users; spine; and
    apparatus applying counteracting forces to thorax torque band ends in order to torque the thorax into a corrective position in relation to the user's head and lower body.

12. The orthopedic device according to claim 11 further comprising a slot, disposed in the band, enabling crossing of the band with one of the ends passing through said slot.

13. The orthopedic device according to claim 11 further comprising two thorax torque bands disposable in a spaced apart relationship around the user's thorax, each band having opposing ends adapted to extend outwardly from the thorax and generally transverse to the user's spine and separate apparatus, corresponding to each band, applying counteracting forces to ends of each band.

14. The orthopedic device according to claim 13 wherein each band includes a slot enabling crossing of the ends of each band with one of the ends of each band passing through a corresponding slot.

15. The orthopedic device according to claim 14 further comprising a thorax vest having loops for guiding each band.

16. The orthopedic device according to claim 14 wherein each band is disposed with the slots adjacent the user's spine in order that the counteracting forces applied to each band cause the user's ribs to be forced toward the spine to push against the spine to correct abdominal posture.

17. The orthopedic device according to claim 13 further comprises at least one pelvic band disposable around a user's pelvis and having ends adapted to extend outwardly from the user's body and generally parallel to a user's spine and connected to the pelvis/leg/feet for applying traction to the user's body.

18. The orthopedic device according to claim 11 wherein said thorax torque band includes a frontal breast accommodating opening.

19. The orthopedic device according to claim 11 wherein the apparatus includes a pair of motorized rollers, each band end being attached to a corresponding roller, each roller wrapping the band thereabout to apply the counteracting forces.

20. The orthopedic device according to claim 11 wherein the apparatus includes a pair of torque arms, each band end being attached to a corresponding torque arm, the torque arms pulling the ends in opposite directions.

21. The orthopedic device according to claim 11 further comprising knee fenders disposed on said pelvis/leg/feet carrier for preventing twisting of the user's lower body.

* * * * *